United States Patent [19]
Müller et al.

[11] Patent Number: 5,203,779
[45] Date of Patent: * Apr. 20, 1993

[54] CATHETER SYSTEM FOR VESSEL RECANALIZATION IN THE HUMAN BODY

[75] Inventors: Gerhard Müller; Hasan Kar; Klaus Dörschel, all of Berlin; Karl-Heinz Schönborn, Mainz, all of Fed. Rep. of Germany

[73] Assignee: Schott Glaswerke, Mainz, Fed. Rep. of Germany

[*] Notice: The portion of the term of this patent subsequent to Nov. 19, 2008 has been disclaimed.

[21] Appl. No.: 788,385

[22] Filed: Nov. 6, 1991

Related U.S. Application Data

[63] Continuation-in-part of Ser. No. 494,743, Mar. 19, 1990, Pat. No. 5,066,292.

[30] Foreign Application Priority Data

Mar. 17, 1989 [DE] Fed. Rep. of Germany ... 8903333[U]

[51] Int. Cl.[5] ............................................. A61M 29/02
[52] U.S. Cl. ............................................. 606/7; 606/15; 606/16; 128/398
[58] Field of Search ............................ 606/2, 7, 10–17; 604/19, 21; 128/639, 6, 395–398; 219/121.6, 121.62

[56] References Cited

U.S. PATENT DOCUMENTS

| | | | |
|---|---|---|---|
| 4,669,467 | 6/1987 | Willett et al. | 606/7 |
| 4,790,310 | 12/1988 | Ginsburg | 606/7 |
| 4,800,876 | 1/1989 | Fox et al. | 606/7 |
| 4,848,336 | 7/1989 | Fox et al. | 606/7 |
| 4,875,897 | 10/1989 | Lee | 606/7 |
| 5,041,108 | 8/1991 | Fox et al. | 606/7 |
| 5,066,292 | 11/1991 | Müller et al. | 606/7 |

OTHER PUBLICATIONS

Fibre Bundle Scanner for Laser Photocoagulation Treatment, Fujii et al, Butteworth & Co, 1982.

*Primary Examiner*—Peter A. Aschenbrenner
*Attorney, Agent, or Firm*—Millen, White, Zelano & Branigan

[57] ABSTRACT

A catheter for vascular surgery includes a circular array of optical fibers therein disposed at the distal end of the catheter with each lightguide being separated by an elastically deformable member with compartments therein for receiving pressurized fluid. Upon pressurizing the compartments the diameter of the catheter expands. The optical fibers are bunched at the end of the catheter proximate the source of laser light where shutters are positioned for selecting only those lightguides at the distal end which are needed to remove blockages. By pressurizing selected elastically expandable members, groups of optical fibers can be isolated from the rest of the optical fibers and deflected toward the wall of the vessel in which the catheter is being used.

7 Claims, 2 Drawing Sheets

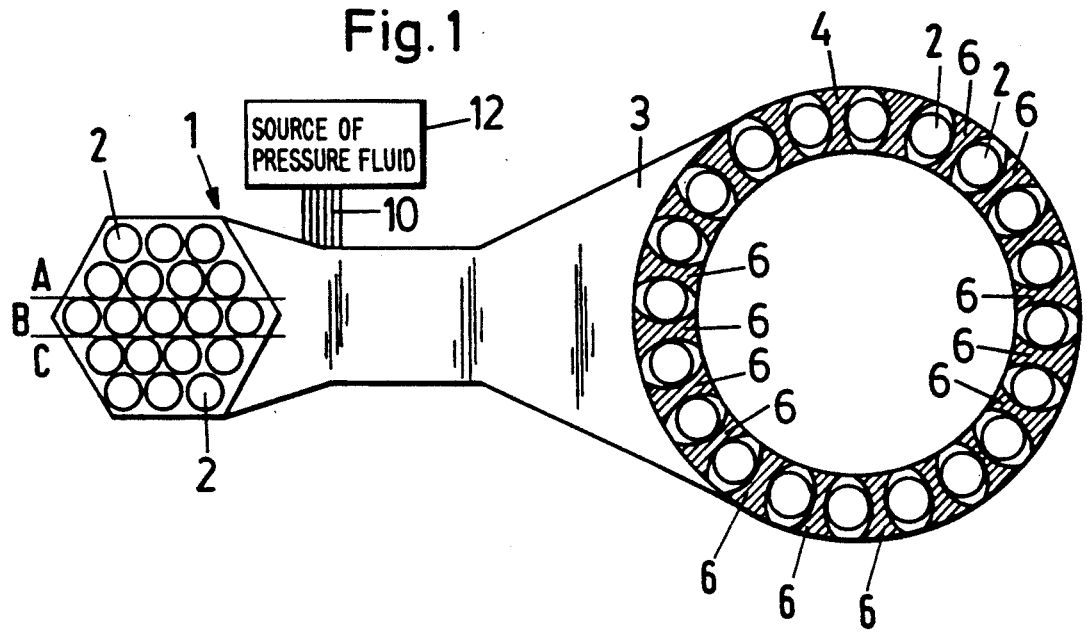
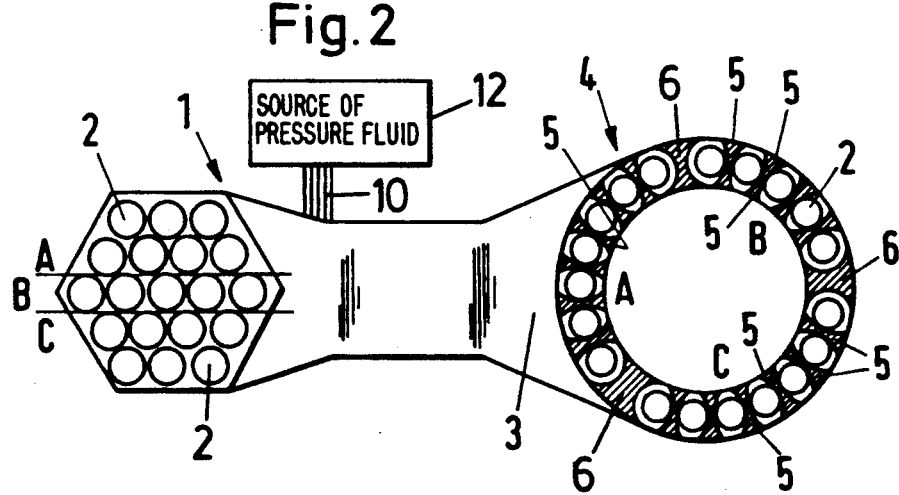

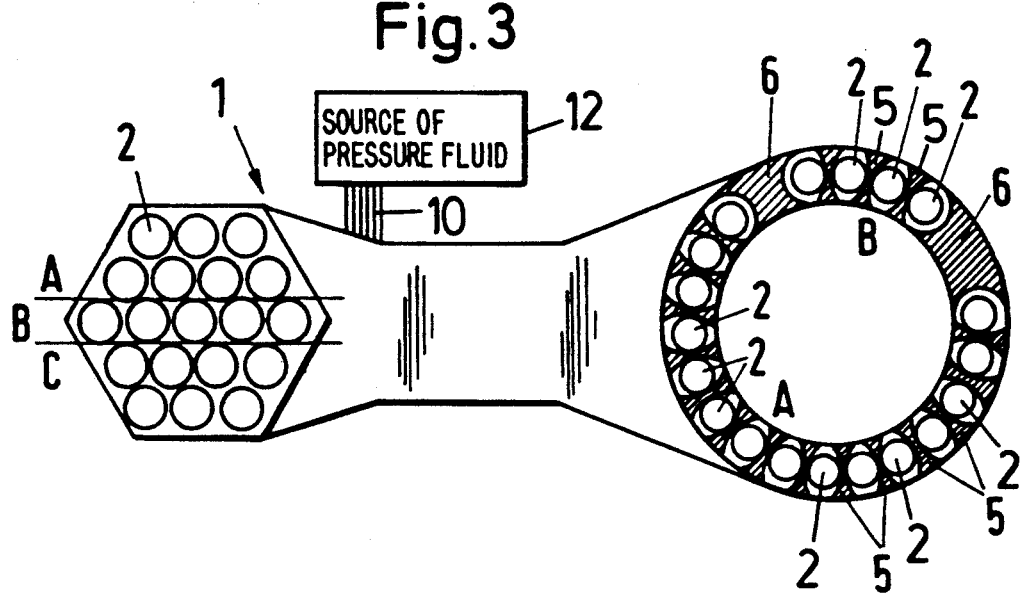
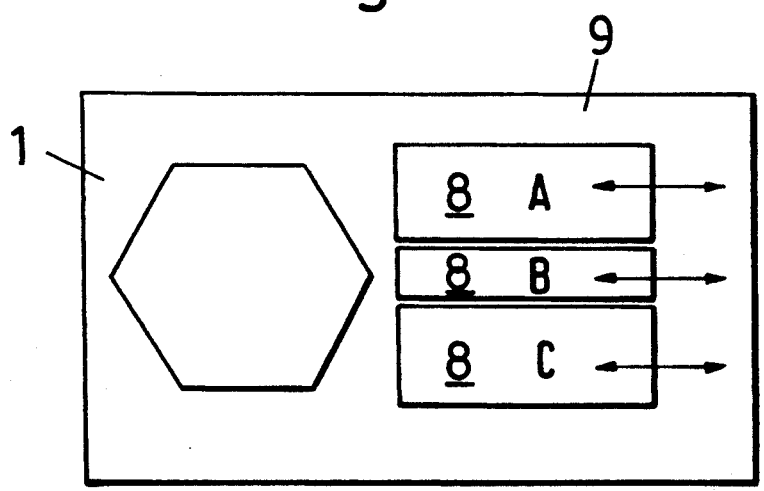

CATHETER SYSTEM FOR VESSEL RECANALIZATION IN THE HUMAN BODY

CROSS-REFERENCE TO RELATED APPLICATION

This application is a continuation-in-part of application Ser. No. 07/494,743, filed Mar. 19, 1990, now U.S. Pat. No. 5,066,292, the disclosure of which is hereby incorporated by reference.

BACKGROUND OF THE INVENTION

The invention relates to a catheter system for the transmission of laser radiation for treatment purposes, especially in vascular systems of the human body. It is known that certain deposits in vascular systems, for example of the human body, especially in blood vessels, can be detached by laser radiation of a certain energy density, presumably as a consequence of the photohydraulic effect, and the thus-treated vessels can therefore be recanalized. A catheter system for such applications has been disclosed, for example, in DOS No. 3,739,965.

Preferably, such catheter systems utilize an annular catheter with an inner duct around which inner duct the wall structure of the catheter retains a circular array of optical fibers for transmitting the laser light to the treatment site at the distal end of the catheter.

It is important in the design of such an annular catheter to ensure that the laser light exiting from the ring-shaped array of optical fibers impinges upon the deposits in the peripheral zone of the vessel which is to be canalized by the laser radiation. Therefore, the diameter of the ring-shaped lightguide arrangement has been chosen, in general, so that the lightguides are located along a peripheral circle corresponding approximately to the deposits. Such a catheter is then introduced into the vessel to be treated up to the point of constriction and can be advanced further only to the extent to which the deposits on the outer wall of the vessel have been removed by the treatment. In order to place the catheter in the right direction with progressing treatment and additional attempts at advancement, the inner duct provided in the catheter, or the lumen, is utilized. Besides being used as a flow channel for rinsing fluid, it can also for the insertion of a thinner guide wire which can be pushed forward even through the as yet untreated constriction sites. It then serves as a guide route for the further advancement of the annular catheter during the course of the treatment.

However, it is not always possible and therefore desirable to employ annular catheters with a diameter already corresponding extensively to the internal diameter of the vessel to be recanalized. It is desirable, especially for guiding a laser catheter forward into regions of a smaller vessel diameter, for example in the lower leg level of a patient or into cardiac coronaries, to utilize lightguide catheters having maximally small diameter which, if at all possible, is to range even below 5 French.

It can be derived, for example, from DOS 3,739,965 that, depending on the optical emergence characteristic of the distal end of the lightguide catheter, the energy density of the laser radiation decreases already with a small distance from the emergence surface to such an extent that it is no longer sufficient for an effective removal of plaques in vessels. This can occur, in particular, when a relatively thin annular catheter is employed; when the deposits to be removed are located asymmetrically on one side, for example in a flaring portion of the vessel; or when such deposits are outside of the diametrical range of the catheter. In such cases, it may become unavoidable to replace the catheter utilized, as required, by a catheter having a larger or smaller internal diameter adapted to the respective lumen of the vessel.

SUMMARY OF THE INVENTION

The invention is based on the object of further developing a catheter system of the type discussed hereinabove in such a way that the diameter of the annular lightguide catheter can be kept at a minimum, but the laser radiation, if needed, can be directed so that it is capable of effectively removing deposits which lie substantially outside of the diameter of the annular catheter.

Elastically expansible connecting members preferably of polymethylsiloxane, between the optical fibers of the lightguide ring make it possible for the lightguides not only to occupy an annular emergence area of a larger diameter, due to a parallel-displacing widening of the ring, but also make it possible to widen the ring of lightguides in a divergent fashion. This latter feature is achieved by means of a gradually increasing elasticity of the connecting material between the optical fibers toward the distal end of the catheter, or, respectively, by limiting the elastic design to only a small longitudinal section before the emergence end of the catheter. Accordingly, the laser radiation emerging from the lightguides is oriented in each case away from the axis of the catheter toward the vessel wall.

Since a single lightguide, however, generally does not carry enough laser energy in order to effect detachment of vessel deposits, a uniform expansion of the ring of lightguides at the distal end of the catheter can lead to an undesirable reduction in the energy density of the radiation due to the increase in the mutual spacing of the individual lightguides. In a preferred embodiment of the invention, the optical fibers can be expanded in groups at the distal end of the catheter system proximate the periphery of the annular catheter. This is achieved by making each of the elastic connecting members between the optical fibers selectively expandable. By expanding only those elastic connecting members between two optical fibers which bound the desired single groups of fibers one from another, while not expanding the elastic connecting members between the optical fibers within the respective fiber groups, selected groups of fibers are chosen. Consequently, the group of several optical fibers which essentially maintain their mutual spacings can be deflected toward the vessel wall. In such a situation, based on the selected group of lightguides, the required energy density remains preserved.

Since the vessel deposits frequently occur in an asymmetrical fashion and consequently only specific regions of the inner vessel wall are to be treated in many cases, it is anyway not always required generally to feed laser light to the entire ring of lightguides. For this purpose the invention furthermore provides that the lightguide fibers are combined, at the proximal inlet end of the annular catheter, into specific groups to which laser light can be supplied selectively. These groups are, of course, preferably identical to the groups of fixedly joined optical fibers at the distal end of the catheter. In order to incur minimum input radiation losses and to avoid destruction of the amount of optical fibers at the proximal end due to laser radiation not coupled into the optical fibers, the fibers at the proximal end of the catheter are preferably arranged in a hexagonally densest packing, these groups of optical fibers forming coherent regional areas of the hexagonal packing. These regional areas can be, for example, parallel area strips of the hexagonal packing. Such strips can be faded out in a simple way by means of parallel sliding stops or the like.

Widening the ring of optical fibers at the distal end of the catheter can be accomplished, for example, by positioning component chambers between the fibers and within the elastically expansible connecting members and distributing the component chambers over the periphery over the annular catheter. The component chambers can be individually supplied with pressurized fluid. With the aid of a selective supply of single component chambers, an expansion of the annular catheter can be effected only in specific peripheral zones wherein, as a consequence, the lightguide fibers can be selectively exposed to laser light.

Inasmuch as the catheters in question are however generally already equipped with an inner duct for other reasons, as mentioned above, the invention provides in a preferred embodiment to include a miniature dilation catheter which can be introduced up to the distal end into the inner duct of the annular catheter and can be expanded at that distal end in order to expand the ring of lightguides in its entirety or in a controlled, radial direction.

There are various possibilities of determining and observing the treatment of only a specific inner wall region by selective activation of optical fibers. Thus, individual ones of the optical fibers of the ring can be utilized for illumination of the treatment site, which latter can then be observed by way of an endoscope inserted in the inner duct of the catheter. It is also possible to recognize, by analysis of radiation reflected from the treatment site, whether there are indeed deposits or tissues of the vessel wall in the intended irradiation zone. Such methods are, however, known in part and are not the subject of this invention. If the expansion of the ring of lightguides at the distal end of the catheter is restricted to only a certain peripheral range, the lightguides can generally be placed into the desired treatment position for the selected range by exerting a rotary force on the catheter, and if necessary, by axial to and fro movements applied at the proximal end or, preferably, by selectively supplying the respective component chambers with pressure fluid.

Owing to the design of the catheter system in accordance with this invention, it is possible, even with the use of a very thin laser ring catheter, to treat regions of a vessel wall by laser irradiation which lie at a distance from the axis of the catheter that can be larger than the radius of the annular catheter. The arrangement of this invention is of advantage even in the case of deposits lying within the peripheral zone of the catheter end since, due to the divergent deflecting ability of the ends of the optical fibers, a higher energy density can be achieved for the detachment of the deposits because in certain cases the procedure can be performed with a steeper angle of incidence of the laser beam onto the site to be treated.

Even on those occasions where laser catheters must be guided forward into regions of smaller vessel diameters, this can be easily realized by means of the arrangement of this invention due to the elastic connections between the optical fibers or fiber groups. In this context, the distal end can be made to approach the vessel deposits without any problems, especially after a repeated, gentle reciprocating motion of the catheter. A change of catheters, as required in most instances in such cases according to the state of the art thus far, is eliminated.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 shows a schematic view of the association of the fiber groups at the distal end with respect to the fiber groups in a hexagonally densest packing at the proximal end of the catheter;

FIG. 2 is a view similar to FIG. 1 showing two groups of fibers being selectively separated from the other fibers;

FIG. 3 is a view similar to FIG. 1 showing a single group of fibers being selectively separated from the other fibers; and FIG. 4 shows a schematic illustration of the sliding stops for fading out the corresponding area strips on the hexagonally densest fiber packing at the proximal end of the catheter.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, if any, cited above and below, and of corresponding application Federal Republic of Germany No. G 89 03 333.7 filed Mar. 17, 1989, are hereby incorporated by reference.

DETAILED DESCRIPTION OF THE DRAWINGS

FIG. 1 illustrates the proximal and distal ends in a schematic view. The proximal end 1 consists of the hexagonally densest packing of the individual optical fibers 2. In the lightguide ring 3 at the distal end 4, the optical fibers 2 are in each case joined into peripheral groups A, B and C, and the individual groups A, B, C are separated one from another by elastically deformable connecting members 6 each comprising a component chamber selectively supplied with pressure fluid.

Referring now to FIG. 2, the respective peripheral groups A, B and C are shown separated from one another at the distal end where the optical fibers 2 of each group are also connected one to another by elastically deformable connecting members 5, each comprising a component chamber which is not supplied with pressure fluid. At the proximal end, the respective regional areas A, B and C of the hexagonally packing can be assigned to their respective peripheral groups A, B and C. In FIG. 2 pressurized fluid has only been applied to three elastically deformable members 6 which are shown expanded and not to deformable connecting members 5.

Referring now to FIG. 3, it is seen that only two elastically deformable members 6 have been pressurized separating only group B as opposed to FIG. 2 wherein the groups A, B and C are each separated by pressurizing three elastically deformable connecting members 6.

These regional areas A, B, C can be optically faded out, by means of the sliding light stops 8 on a coupler 9 for a laser light source represented in FIG. 4, individually or respectively in twos at the same time, so that respectively only one or two fiber groups A, B, C are exposed to laser light at the distal end.

The feed channels 10 for pressure fluid from a source of pressure fluid 12 and the distending means in the distal end zone 4 can be integrated directly in the fiber ring of the catheter whereby the distensible pressure chambers within the elastic connecting sections 6 lie directly between the optical fibers 2 in the distal end zone. Consequently, with pressure being selectively exerted on pressure chambers 6 that can be selected at will, an interposed zone with non-expanded connecting members 5 between the optical fibers 2 can be selectively bent away toward the vessel wall.

If necessary or desired, it is possible with the structure of the instant invention to isolate a single optical fiber 2 by supplying pressurized fluid to the compartments within the elastically deformable members 6 disposed on opposite sides of that individual optical fiber. However, for most situations, groups or a group of optical fibers 2 are isolated and deflected as is shown in FIGS. 2 and 3.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A catheter system having a proximal end and a distal light emitting end for the transmission of laser radiation for treatment purposes, comprising an array of lightguides comprised of optical fibers arranged in the catheter wall structure each light guide having proximal ends and distal light emitting ends, means for coupling a laser light source to the proximal ends of the lightguides, the light guides being arranged as a ring of lightguides of an initial circumference at the distal light-emitting end of the catheter with the light guides being connected to one another by elastically extendable material for allowing enlargement of the circumference of the distal end, the enlargement in circumference being selectively accomplished by increasing the spacing between the individual light guides of the ring and between specific peripheral groups of light guides of the ring.

2. The catheter system according to claim 1, wherein the elastically extendable material is polymethylsiloxane.

3. The catheter system according to claim 1, wherein expansion chambers which can be supplied with pressurized fluid through the catheter are provided between individual light guides for expanding the ring of light guides at the distal end of the catheter.

4. The catheter system according to claim 3, wherein the expansion chamber means comprises component chambers which can be separately activated and expand in different radial directions.

5. The catheter system according to claim 1, wherein the means for coupling laser light into the proximal ends of the lightguides include selectively operable regional shutters which selectively cover the proximal ends to block transmission of light through the lightguides so that, specific groups of lightguides can be supplied with laser light, the specific groups being identical to the peripheral groups of optical fibers are at the distal end of the catheter.

6. The catheter system according to claim 5, wherein the lightguides are gathered at the proximal end in a hexagonally maximally dense packing array for coupling with the laser light source, and wherein the groups of lightguides at the distal end of the array, are identified with coherent regional areas in the hexagonal packing array.

7. The catheter system of claim 1 wherein the catheter is useful in treating human vascular systems.

* * * * *